(12) United States Patent
Wang et al.

(10) Patent No.: US 12,384,745 B2
(45) Date of Patent: Aug. 12, 2025

(54) CRYSTAL FORM OF FIVE-MEMBERED N HETEROCYCLIC COMPOUND, AND APPLICATION THEREOF

(71) Applicant: CHIA TAI TIANQING PHARMACEUTICAL GROUP CO., LTD., Lianyungang (CN)

(72) Inventors: Pujun Wang, Lianyungang (CN);
Meng Guo, Lianyungang (CN);
Mingtong Hu, Lianyungang (CN); Jie Wu, Lianyungang (CN); Wangwei Ao, Lianyungang (CN); Yinsheng Zhang, Lianyungang (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 813 days.

(21) Appl. No.: 17/763,114

(22) PCT Filed: Sep. 28, 2020

(86) PCT No.: PCT/CN2020/118426
§ 371 (c)(1),
(2) Date: Mar. 23, 2022

(87) PCT Pub. No.: WO2021/058001
PCT Pub. Date: Apr. 1, 2021

(65) Prior Publication Data
US 2022/0332684 A1 Oct. 20, 2022

(30) Foreign Application Priority Data
Sep. 29, 2019 (CN) .......................... 201910933542.7

(51) Int. Cl.
*C07D 207/34* (2006.01)
(52) U.S. Cl.
CPC ........ *C07D 207/34* (2013.01); *C07B 2200/13* (2013.01)
(58) Field of Classification Search
CPC .......................... C07D 207/34; C07B 2200/13
See application file for complete search history.

(56) References Cited

U.S. PATENT DOCUMENTS

| 11,597,716 B2 | 3/2023 | Zhang et al. |
| 2016/0176817 A1 | 6/2016 | Vandyck et al. |
| 2021/0017154 A1* | 1/2021 | Zhang ................ A61K 31/4439 |
| 2022/0185774 A1 | 6/2022 | Zhang et al. |
| 2022/0363634 A1 | 11/2022 | Lu et al. |

FOREIGN PATENT DOCUMENTS

| CN | 101756890 | 6/2010 |
| CN | 102389400 | 3/2012 |
| CN | 103705478 | 4/2014 |
| CN | 105431413 A | 3/2016 |
| CN | 105658624 A | 6/2016 |
| CN | 105980378 | 9/2016 |
| CN | 105431413 | 1/2018 |
| CN | 105658624 | 1/2019 |
| CN | 109153640 A | 1/2019 |
| CN | 109790168 A | 5/2019 |
| CN | 107721895 | 3/2020 |
| RU | 2470916 | 12/2012 |
| WO | WO 2006012642 A2 | 2/2006 |
| WO | WO2014184350 | 11/2014 |
| WO | WO2015011281 | 1/2015 |
| WO | WO2017156255 | 9/2017 |
| WO | WO2018039531 | 3/2018 |
| WO | WO2018050110 | 3/2018 |
| WO | WO2019165374 | 8/2019 |
| WO | WO 2019165374 A1 | 8/2019 |
| WO | WO2019185016 | 10/2019 |
| WO | WO 2019185016 A1 | 10/2019 |
| WO | WO2019241292 | 12/2019 |
| WO | WO 2020151252 A1 | 7/2020 |
| WO | WO 2020156494 | 8/2020 |

(Continued)

OTHER PUBLICATIONS

International Search Report and Written Opinion in International Appln. No. PCT/CN2019/108483, dated Jan. 2, 2020, 28 pages.
International Search Report and Written Opinion in PCT/CN2020/118426, mailed on Jan. 5, 2021, 22 pages.
International Preliminary Report on Patentability in International Appln. No. PCT/CN2022/123799, mailed Apr. 18, 2024, 16 pages (with English Translation).
International Search Report and Written Opinion in International Appln. No. PCT/CN2022/123799, mailed Dec. 15, 2022, 21 pages (with English Translation).
Njampatnam et al., "Recent advances in the development of HBV capsid assembly modulators," Current Opinions in Chemical Biology, Jun. 2019, 50:73-79.
Alekseyev, V.V., "Optical Isomerism and Drugs Pharmacological Activity," Soros Educational Journal, 1998, pp. 49-55 (8 pages).

(Continued)

*Primary Examiner* — Timothy R Rozof
(74) *Attorney, Agent, or Firm* — Fish & Richardson P.C.

(57) ABSTRACT

Disclosed are a crystalline form of a five-membered N heterocyclic compound, particularly, a crystalline form of a compound as represented by formula I, and an application of the crystalline form in preparation of a medication for preventing or treating a disease benefiting from inhibition of capsid protein assembly.

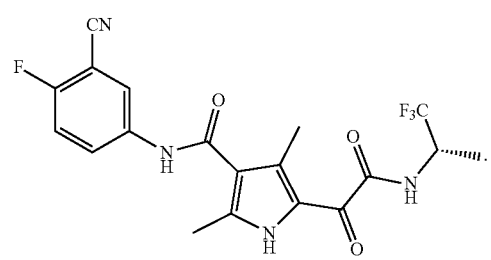

16 Claims, 1 Drawing Sheet

(56) References Cited

FOREIGN PATENT DOCUMENTS

| WO | WO 2021058002 | 4/2021 |
|---|---|---|
| WO | WO 2021119081 | 6/2021 |

OTHER PUBLICATIONS

Knunyants, I.L., "Chemical Encyclopedic Dictionary," Moscow, Soviet Encyclopedia, 1983, pp. 130-131.

Kummerer, Klaus, "Pharmaceuticals in the Environment," Annu. Rev. Environ. Resourc., 2010, 35:57-75.

RU Office Action in Russian Appln. No. 2021123614/04, dated Feb. 28, 2023, 27 pages (with English translation).

Office Action in U.S. Appl. No. 17/425,701, mailed on Jun. 3, 2024, 37 pages.

Testa, "Prodrug research: futile or fertile?" Biochemical Pharmacology, 2004, 68:2097-2106.

CN Office Action in Chinese Appln. No. 202080066483.9, dated Oct. 13, 2023, 10 pages (with English translation).

International Search Report and Written Opinion in PCT/CN2020/118426, filed Sep. 28, 2019.

JP Office Action in Japanese Appln. No. 2021-542370, dated Oct. 3, 2023, 9 pages (with English translation).

Nozaki et al., "Medicinal Drug Chemistry (Soyaku Kagaku)," 1st ed., Jul. 1, 1995, Chapter 5.2.2, pp. 98-99 (with English abstract).

PubMed CID 2969881, "2-Amino-9-[(1S,3R,4S)-4-hydr-oxy-3-hydroxy-methyl-2-methyl-enecyclo-pent-yl]-1,9-dihydro-6H-purin-6-one monohydrate," Aug. 26, 2009, retrieved on Oct. 22, 2024, retrieved from URL <https://pubmed.ncbi.nlm.nih.gov/21577631/>, 10 pages.

PubMed CID 464205, "(R)-9-(2-Phosphonomethoxypropyl)adenine," Aug. 1, 2005, retrieved Oct. 22, 2024, retrieved from URL <https://pubchem.ncbi.nlm.nih.gov/compound/464205>, 54 pages.

Brahmania, et al., "New therapeutic agents for chronic hepatitis B," The Lancet Infectious Diseases, Jan. 13, 2016, 16(2):e10-e21.

Extended European Search Report in European Appln No. 19777163.7, dated Nov. 25, 2021, 7 pages.

Greene's Protective Groups in Organic Synthesis, 4th ed., Wuts and Greene (eds)., Apr. 2006, Chapter 2, 351 pages.

He et al., "Hepatitis B virus replication mechanisms and drug targets of chronic hepatitis B," Chinese Pharmacological Bulletin, Feb. 2015, 31(2):152-156 (with English abstract).

International Preliminary Report on Patentability in International Appln. No. PCT/CN2019/108483, dated Aug. 5, 2021, 17 pages (with English translation).

International Preliminary Report on Patentability in International Appln. No. PCT/CN2020/118426, dated Mar. 15, 2022, 13 pages (with English translation).

International Search Report and Written Opinion in International Appln. No. PCT/CN2019/108483, dated Jan. 2, 2020, 12 pages.

Office Action in Eurasian Appln. No. 202092159, dated Sep. 17, 2021, 7 pages (with English translation).

\* cited by examiner

CRYSTAL FORM OF FIVE-MEMBERED N HETEROCYCLIC COMPOUND, AND APPLICATION THEREOF

CROSS-REFERENCE TO RELATED APPLICATIONS

The present application is a National Stage Application of International Application No. PCT/CN2020/118426, filed Sep. 28, 2020, which claims priority and benefit to the Chinese Patent Application No. 201910933542.7, filed with National Intellectual Property Administration, PRC on Sep. 29, 2019, the disclosure of which is incorporated herein by reference in its entirety.

TECHNICAL FIELD

The present application relates to a crystalline form of a five-membered N heterocyclic compound, and in particular, to a crystalline form of a compound of formula I. The present application also relates to use of the crystalline form in preparing a medicament for preventing or treating a disease benefiting from the inhibition of capsid protein assembly.

BACKGROUND

Currently, since there is only control for chronic viral hepatitis B rather than curative measures, treatments are restricted to two groups of agents (interferon and nucleoside analogues/inhibitors of viral polymerase). The low cure rate of HBV is partly due to the presence and persistence of covalently closed circular DNA (cccDNA) in the nuclei of infected hepatocytes. Current treatments cannot eliminate the cccDNA in the reservoir, while some new targets of HBV, such as core inhibitors (e.g., inhibitors of viral capsid protein formation or assembly, cccDNA inhibitors and activators of interferon-stimulated genes, etc.), are promising for curing hepatitis B (Mayur Brahmania, et al., New therapeutic agents for chronic hepatitis B). The HBV capsid is assembled from the core protein, and before reverse transcription, HBV reverse transcriptase and pgRNA should be correctly encapsulated by the capsid protein. Thus, blocking capsid protein assembly or accelerating capsid protein degradation can block the process of capsid protein assembly, thereby affecting virus replication.

BRIEF SUMMARY

In one aspect, the present application provides a crystal of a compound of formula I,

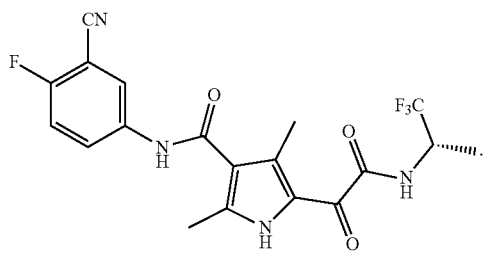

I

In another aspect, the present application provides a crystalline form composition, wherein the crystal of the compound of formula I accounts for 50% or more, preferably 80% or more, more preferably 90% or more and most preferably 95% or more of the weight of the crystalline form composition.

In another aspect, the present application provides a pharmaceutical composition comprising a therapeutically effective amount of the crystal of the compound of formula I or the crystalline form composition thereof disclosed herein.

In still another aspect, the present application also provides use of the crystal of the compound of formula I, the crystalline form composition thereof or the pharmaceutical composition thereof disclosed herein in preparing a medicament for preventing or treating a disease benefiting from the inhibition of capsid protein assembly.

In still another aspect, the present application also provides use of the crystal of the compound of formula I, the crystalline form composition thereof or the pharmaceutical composition thereof disclosed herein in preparing a medicament for preventing or treating hepatitis B virus infection.

In still another aspect, the present application also provides use of the crystal of the compound of formula I, the crystalline form composition thereof or the pharmaceutical composition thereof disclosed herein in preventing or treating a disease benefiting from the inhibition of capsid protein assembly.

In still another aspect, the present application also provides a method for treating a disease benefiting from the inhibition of capsid protein assembly, comprising administering to a mammal in need of such treatment a therapeutically effective amount of the crystal of the compound of formula I, the crystalline form composition thereof or the pharmaceutical composition thereof disclosed herein.

In still another aspect, the present application also provides the crystal of the compound of formula I, the crystalline form composition thereof or the pharmaceutical composition thereof disclosed herein for use in preventing or treating a disease benefiting from the inhibition of capsid protein assembly.

SUMMARY

Figure 1:
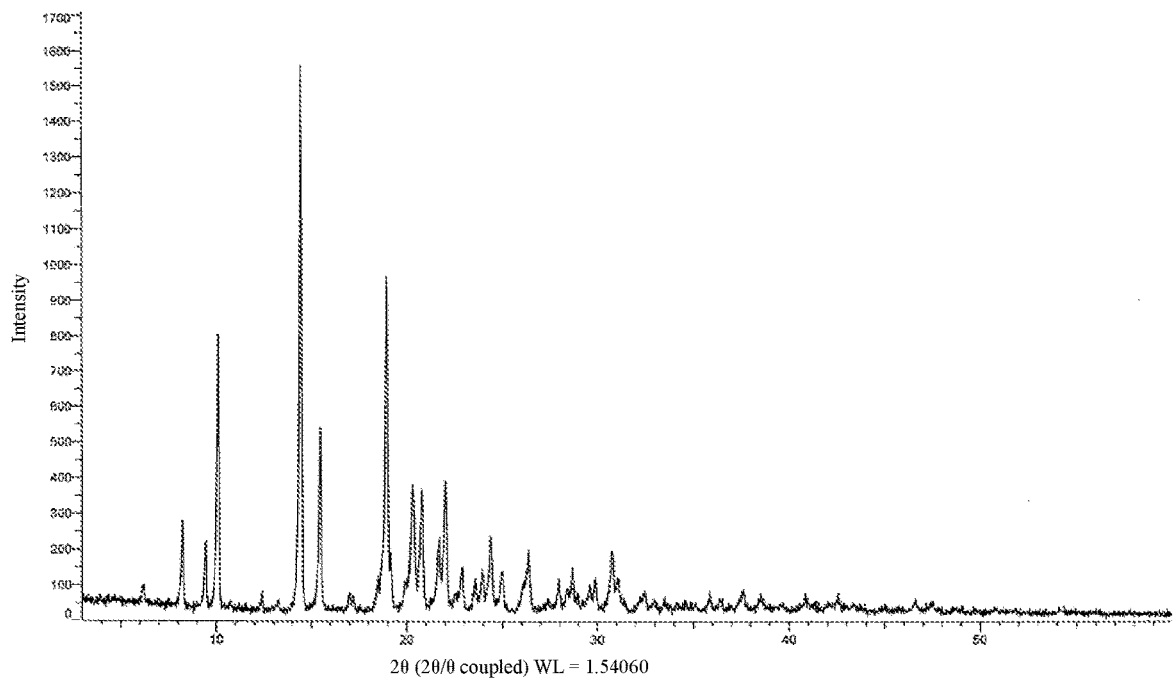
FIG. 1 is an XRPD pattern of a crystalline form A of the compound of formula I.

In one aspect, the present application provides a crystal of a compound of formula I,

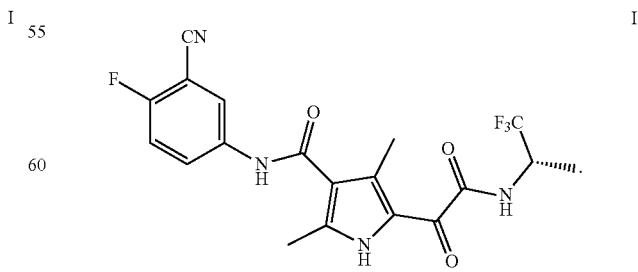

I

In another aspect, the present application provides a crystalline form A of the compound of formula I described above having characteristic diffraction peaks in an X-ray powder diffraction pattern at the following 2θ angles: 8.25±0.20°, 10.10±0.20°, 14.46±0.20°, 15.48±0.20° and 18.97±0.20°; in some embodiments of the present application, the crystalline form A described above has characteristic diffraction peaks in an X-ray powder diffraction pattern at the following 2θ angles: 8.25±0.20°, 9.46±0.20°, 10.10±0.20°, 14.46±0.20°, 15.48±0.20°, 18.97±0.20°, 20.33±0.20° and 22.02±0.20°; in some embodiments of the present application, the crystalline form A described above has characteristic diffraction peaks in an X-ray powder diffraction pattern at the following 2θ angles: 8.25±0.20°, 9.46±0.20°, 10.10±0.20°, 14.46±0.20°, 15.48±0.20°, 18.97±0.20°, 20.33±0.20°, 20.80±0.20°, 21.67±0.20°, 22.02±0.20°, 24.37±0.20°, 26.37±0.20° and 30.77±0.20°; in some embodiments of the present application, the crystalline form A described above has characteristic diffraction peaks in an X-ray powder diffraction pattern at the following 2θ angles: 8.25±0.20°, 9.46±0.20°, 10.10±0.20°, 14.46±0.20°, 15.48±0.20°, 18.97±0.20°, 20.33±0.20°, 20.80±0.20°, 21.67±0.20°, 22.02±0.20°, 22.88±0.20°, 23.93±0.20°, 24.37±0.20°, 24.97±0.20°, 26.37±0.20°, 28.68±0.20° and 30.77±0.20°.

In some embodiments of the present application, the positions and relative intensities of diffraction peaks in the XRPD pattern of the crystalline form A described above are shown in Table 1 below:

TABLE 1

XRPD data for crystalline form A

| No. | 2θ (±0.20°) | Relative intensity (%) |
| --- | --- | --- |
| 1 | 6.18 | 3.1 |
| 2 | 8.25 | 14.9 |
| 3 | 9.46 | 11.8 |
| 4 | 10.10 | 51.1 |
| 5 | 12.39 | 3.2 |
| 6 | 14.46 | 100.0 |
| 7 | 15.48 | 32.6 |
| 8 | 18.97 | 60.3 |
| 9 | 19.96 | 4.4 |
| 10 | 20.33 | 22.7 |
| 11 | 20.80 | 21.5 |
| 12 | 21.67 | 12.1 |
| 13 | 22.02 | 22.7 |
| 14 | 22.88 | 6.9 |
| 15 | 23.58 | 4.6 |
| 16 | 23.93 | 6.6 |
| 17 | 24.37 | 13.4 |
| 18 | 24.97 | 7.2 |
| 19 | 26.37 | 10.5 |
| 20 | 27.95 | 4.6 |
| 21 | 28.40 | 3.3 |
| 22 | 28.68 | 6.5 |
| 23 | 29.61 | 3.6 |
| 24 | 29.89 | 4.8 |
| 25 | 30.77 | 10.8 |
| 26 | 31.07 | 5.4 |
| 27 | 32.49 | 3.2 |
| 28 | 37.62 | 2.9 |

In some embodiments of the present application, the X-ray powder diffraction pattern(XRPD) of the crystalline form A described above is shown in FIG. 1.

In some embodiments of the present application, the crystalline form A described above has a differential scanning calorimetry (DSC) curve having an endothermic peak at 227.34±5° C.

In some embodiments of the present application, the DSC pattern of the crystalline form A described above is shown in FIG. 2.

In still another aspect, the present application provides a method for preparing the crystalline form A, the method comprising:
adding the compound of formula I described above to a solvent, and separating a solid.

In some embodiments of the present application, the method for preparing crystalline form A described above comprises the following steps: adding the compound of formula I described above to a solvent, crystallizing and separating the solid.

In some embodiments of the present application, in the method for preparing the crystalline form A described above, the volume-to-mass ratio of the solvent to the compound of formula I is 1 mL-400 mL/g; in some embodiments, the volume-to-mass ratio of the solvent to the compound of formula I is 5 mL-250 mL/g; in some embodiments, the volume-to-mass ratio of the solvent to the compound of formula I is 10 mL-220 mL/g; in some embodiments, the volume-to-mass ratio of the solvent to the compound of formula I is 10 mL/g, 20 mL/g, 30 mL/g, 40 mL/g, 50 mL/g, 60 mL/g, 70 mL/g, 80 mL/g, 90 mL/g, 100 mL/g, 110 mL/g, 120 mL/g, 130 mL/g, 140 mL/g, 150 mL/g, 160 mL/g, 170 mL/g, 180 mL/g, 190 mL/g, 200 mL/g, 210 mL/g, 220 mL/g or within a range formed by any of the ratios; in some embodiments, the volume-to-mass ratio of the solvent to the compound of formula I is 10 mL/g, 50 mL/g or 220 mL/g.

In some embodiments of the present application, in the method for preparing the crystalline form A described above, the solvent is selected from the group consisting of mixtures of one or more of methanol, acetonitrile, tetrahydrofuran or water. In some embodiments of the present application, in the method for preparing the crystalline form A described above, the solvent is selected from the group consisting of methanol, a mixture of acetonitrile and water or a mixture of tetrahydrofuran and water.

In some embodiments of the present application, the volume-to-mass ratio of methanol to the compound of formula I is 10-100 mL/g; in some embodiments of the present application, the volume-to-mass ratio of methanol to the compound of formula I is 10 mL/g, 20 mL/g, 30 mL/g, 40 mL/g, 50 mL/g, 60 mL/g, 70 mL/g, 80 mL/g, 90 mL/g, 100 mL/g or within a range formed by any of the ratios; in some embodiments of the present application, the volume-to-mass ratio of methanol to the compound of formula I is 10-50 mL/g; in some embodiments of the present application, the volume-to-mass ratio of methanol to the compound of formula I is 50 mL/g.

In some embodiments of the present application, the volume ratio of acetonitrile to water is 1:1-10:1; in some embodiments of the present application, the volume ratio is 1:1, 2:1, 3:1, 4:1, 5:1, 6:1, 7:1, 8:1, 9:1, 10:1 or within a range formed by any of the ratios; in some embodiments of the present application, the volume ratio is 2:1-5:1; in some embodiments of the present application, the volume ratio is 3.4:1.

In some embodiments of the present application, the volume ratio of tetrahydrofuran to water is 1:1-1:10; in some embodiments of the present application, the volume ratio is 1:1, 1:2, 1:3, 1:4, 1:5, 1:6, 1:7, 1:8, 1:9, 1:10 or within a range formed by any of the ratios; in some embodiments of the present application, the volume ratio is 1:1-1:5; in some embodiments of the present application, the volume ratio is 1:5.

In some embodiments of the present application, in the method for preparing the crystalline form A described above, the means for separating the solid is selected from filtration.

In some embodiments of the present application, the method for preparing the crystalline form A described above comprises: adding the compound of formula I described above to a solvent, and stirring to give a clarified solution or optionally, heating to give a clarified solution; in some specific embodiments, the mixture is heated to 50-80° C.; in some specific embodiments, the mixture is heated to 60° C.

In some embodiments of the present application, the method for preparing the crystalline form A described above optionally comprises cooling to room temperature and/or cooling in an ice-water bath for crystallization, and/or optionally adding water for crystallization.

In the present application, XRPD is performed by a Bruker D8 ADVANCE X-ray powder diffractometer, light tube: Cu, k α(λ=1.54056 Å), light tube voltage: 40 kV, light tube current: 40 mA; scattering slit: 0.618 mm; scanning range: 3-60 deg; step size: 0.02 deg; step time: 0.1 s.

In the present application, DSC is performed by a Mettler DSC 1 differential scanning calorimeter, temperature range: 50-300° C., heating rate: 10.00 K/min.

In another aspect, the present application provides a crystalline form composition, wherein the crystal of the compound of formula I disclosed herein accounts for 50% or more, preferably 80% or more, more preferably 90% or more and most preferably 95% or more of the weight of the crystalline form composition.

In another aspect, the present application provides a crystalline form composition comprising the crystalline form A disclosed herein, wherein the crystalline form A accounts for 50% or more, preferably 80% or more, more preferably 90% or more and most preferably 95% or more of the weight of the crystal form composition.

In another aspect, the present application provides a pharmaceutical composition comprising a therapeutically effective amount of the crystal of the compound of formula I or the crystalline form composition thereof disclosed herein. The pharmaceutical composition disclosed herein may or may not contain a pharmaceutically acceptable excipient. In addition, the pharmaceutical composition disclosed herein may further comprise one or more additional therapeutic agents.

In still another aspect, the present application also provides use of the crystal of the compound of formula I, the crystalline form composition thereof or the pharmaceutical composition thereof disclosed herein in preparing a medicament for preventing or treating a disease benefiting from the inhibition of capsid protein assembly.

In still another aspect, the present application also provides use of the crystal of the compound of formula I, the crystalline form composition thereof or the pharmaceutical composition thereof disclosed herein in preparing a medicament for preventing or treating hepatitis B virus infection.

In still another aspect, the present application also provides use of the crystal of the compound of formula I, the crystalline form composition thereof or the pharmaceutical composition thereof disclosed herein in preventing or treating a disease benefiting from the inhibition of capsid protein assembly.

In still another aspect, the present application also provides a method for preventing or treating a disease benefiting from the inhibition of capsid protein assembly, comprising administering to a mammal, preferably a human, in need of such treatment or prevention a therapeutically effective amount of the crystal of the compound of formula I, the crystalline form composition thereof or the pharmaceutical composition thereof disclosed herein.

In still another aspect, the present application also provides the crystal of the compound of formula I, the crystalline form composition thereof or the pharmaceutical composition thereof disclosed herein for use in preventing or treating a disease benefiting from the inhibition of capsid protein assembly.

In some embodiments of the present application, the disease benefiting from the inhibition of capsid protein assembly is a disease caused by hepatitis B virus (HBV) infection.

In some embodiments of the present application, the disease benefiting from the inhibition of capsid protein assembly is a liver disease caused by hepatitis B virus (HBV) infection.

In some embodiments of the present application, the prevention or treatment of the disease benefiting from the inhibition of capsid protein assembly refers to control, reduction or elimination of HBV to prevent, alleviate or cure a liver disease in an infected patient.

Definitions and Description

Unless otherwise stated, the following terms and phrases used herein are intended to have the following meanings. A particular phrase or term, unless otherwise specifically defined, should not be considered as uncertain or unclear, but construed according to its common meaning. When referring to a trade name, it is intended to refer to its corresponding commercial product or its active ingredient.

It should be noted that in the X-ray powder diffraction pattern, the position and relative intensity of a peak may vary due to measuring instruments, measuring methods/conditions, and other factors. For any specific crystalline form, the position of a peak may have an error, and the measurement of 2θ may have an error of ±0.20°. Therefore, this error should be considered when determining each crystalline form, and crystalline forms within this margin of error are within the scope of the present application.

It should be noted that, for the same crystalline form, the position of an endothermic peak in the DSC pattern may vary due to measuring instruments, measuring methods/conditions, and other factors. For any specific crystalline form, the position of an endothermic peak may have an error of ±5° C. or ±3° C. Therefore, this error should be considered when determining each crystalline form, and crystalline forms within this margin of error are within the scope of the present application.

The word "comprise" and variations thereof such as "comprises" or "comprising" will be understood in an open, non-exclusive sense, i.e., "including but not limited to".

The term "pharmaceutically acceptable excipient" refers to an inert substance administered with active ingredient to facilitate administration of the active ingredient, including, but not limited to, any glidant, sweetener, diluent, preservative, dye/coloring agent, flavor enhancer, surfactant, wetting agent, dispersant, disintegrant, suspending agent, stabilizer, isotonizing agent, solvent or emulsifier acceptable for use in humans or animals (e.g., domesticated animals) as permitted by the National Medical Products Administration, PRC. Non-limiting examples of the excipients include calcium carbonate, calcium phosphate, various sugars and types of starch, cellulose derivatives, gelatin, vegetable oils, and polyethylene glycols.

The term "pharmaceutical composition" refers to a mixture consisting of one or more of the compounds or pharmaceutically acceptable salts thereof disclosed herein and a pharmaceutically acceptable excipient. The pharmaceutical composition is intended to facilitate the administration of the compound to an organic entity.

The pharmaceutical composition disclosed herein can be prepared by combining the compound disclosed herein with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere, and aerosol.

Typical routes of administration of the crystalline form, crystalline form composition or the pharmaceutical composition thereof disclosed herein include, but are not limited to, oral, rectal, topical, inhalation, parenteral, sublingual, intravaginal, intranasal, intraocular, intraperitoneal, intramuscular, subcutaneous and intravenous administrations.

The pharmaceutical composition disclosed herein can be manufactured by methods well known in the art, such as conventional mixing, dissolving, granulating, dragée-making, levigating, emulsifying, and lyophilizing.

In some embodiments, the pharmaceutical composition is in an oral form. For oral administration, the pharmaceutical composition can be formulated by mixing the active compounds with pharmaceutically acceptable excipients well known in the art. These excipients enable the compounds disclosed herein to be formulated into tablets, pills, pastilles, dragées, capsules, liquids, gels, slurries, suspensions and the like for oral administration to a patient.

Therapeutic dosages of the compounds disclosed herein may be determined by, for example, the specific use of a treatment, the route of administration of the compound, the health and condition of a patient, and the judgment of a prescribing physician. The proportion or concentration of the compound disclosed herein in a pharmaceutical composition may not be constant and depends on a variety of factors including dosages, chemical properties (e.g., hydrophobicity), and routes of administration.

The term "treat" or "treatment" means administering the compound or formulation described herein to ameliorate or eliminate a disease or one or more symptoms associated with the disease, and includes:
 (i) inhibiting a disease or disease state, i.e., arresting its development; and
 (ii) alleviating a disease or disease state, i.e., causing its regression.

The term "prevent" or "prevention" means administering the compound or formulation described herein to prevent a disease or one or more symptoms associated with the disease, and includes: preventing the occurrence of the disease or disease state in a mammal, particularly when such a mammal is predisposed to the disease state but has not yet been diagnosed with it.

For drugs and pharmacological active agents, the term "therapeutically effective amount" refers to an amount of a drug or a medicament that is sufficient to provide the desired effect but is non-toxic. The determination of the effective amount varies from person to person. It depends on the age and general condition of a subject, as well as the particular active substance used. The appropriate effective amount in a case may be determined by those skilled in the art in the light of routine tests.

The therapeutically effective amount of the crystalline form disclosed herein is from about 0.0001 to 20 mg/kg body weight (bw)/day, for example from 0.001 to 10 mg/kg bw/day.

The dosage frequency of the crystalline form disclosed herein depends on needs of an individual patient, e.g., once or twice daily or more times daily. Administration may be intermittent, for example, in a period of several days, the patient receives a daily dose of the crystalline form disclosed herein, and in a following period of several days or more days, the patient does not receive the daily dose of the crystalline form disclosed herein.

All solvents used in the present application are commercially available and can be used without further purification.

The following abbreviations are used herein: DMF for N,N-dimethylformamide; EA for ethyl acetate; MeOH for methanol; DMSO for dimethyl sulfoxide; HATU for 2-(7-benzotriazole oxide)-N,N,N',N'-tetramethyluronium hexafluorophosphate; DIPEA for N,N-diisopropylethylamine.

Technical Effects

The crystalline form of the present application has good pharmacological activity and good stability under conditions of high humidity, high temperature or illumination, demonstrating good pharmaceutical properties and high druggability prospect.

DETAILED DESCRIPTION

The present application is described in detail below by way of examples. However, this is by no means disadvantageously limiting the scope of the present application. Although the present application has been described in detail herein and specific embodiments have also been disclosed, it will be apparent to those skilled in the art that various changes and modifications can be made to the specific embodiments without departing from the spirit and scope of the present application.

Example 1. Preparation of Compound of Formula I

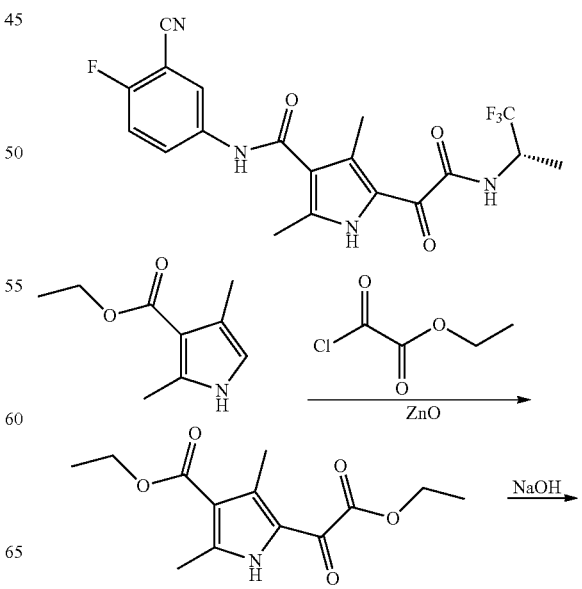

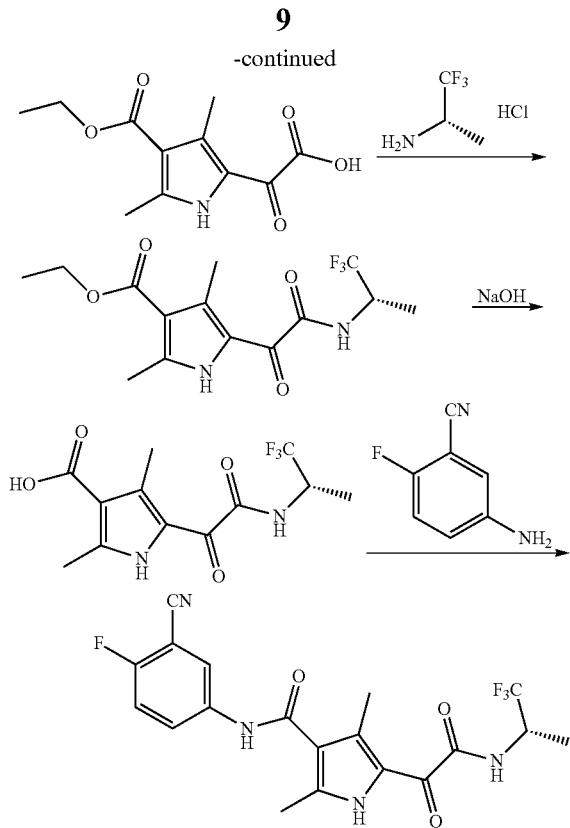

Step A: Ethyl 2-chloro-2-oxoacetate (40.8 g) and zinc oxide (1.22 g) were sequentially added to a reaction flask in an ice bath under $N_2$ atmosphere, then ethyl 2,4-dimethyl-1H-pyrrol-3-carboxylate (5 g) was added. After the addition, the reaction system was stirred in an ice bath for 10 min, the ice bath was removed, and then stirred at room temperature. After the reaction was completed, the mixture was slowly and dropwise added to 200 mL of ice-water mixture, followed by addition of EA (200 mL). The mixture was separated, and the organic phase was dried over anhydrous sodium sulfate, concentrated and subjected to preparative column chromatography to obtain ethyl 5-(2-ethoxy-2-oxoacetyl)-2,4-dimethyl-1H-pyrrol-3-carboxylate (4.5 g). MS (ESI+, [M+Na]$^+$) m/z: 290.07.

Step B: Ethyl 5-(2-ethoxy-2-oxoacetyl)-2,4-dimethyl-1H-pyrrol-3-carboxylate (3.5 g) and MeOH (40 mL) were sequentially added to a reaction flask, then a solution of sodium hydroxide (1.05 g) in water (20 mL) was added dropwise in an ice bath. The reaction system was stirred at room temperature. After the reaction was completed, the aqueous phase was adjusted to pH 3-4 by adding 2 N aqueous hydrochloric acid solution. EA (100 mL×2) was added for extraction, and the organic phase was washed with water (30 mL) and concentrated to obtain 2-(4-(ethoxycarbonyl)-3,5-dimethyl-1H-pyrrol-2-yl)-2-oxoacetic acid (2.7 g). MS (ESI-,[M–H]$^-$) m/z: 238.1.

Step C: 2-(4-(Ethoxycarbonyl)-3,5-dimethyl-1H-pyrrol-2-yl)-2-oxoacetic acid (1 g), DMF (20 mL), HATU (2.07 g) and DIPEA (1.08 g) were sequentially added to a reaction flask at room temperature. After the addition, the reaction system was stirred at room temperature for 10 min, then (S)-1,1,1-trifluoropropan-2-amine hydrochloride (0.63 g) was added. After the reaction was completed, the reaction mixture was poured into 50 mL of water and extracted with EA (50 mL×3). The organic phase was washed with satu- rated aqueous sodium sulfate solution (50 mL×3), dried over anhydrous sodium sulfate and filtered. The filtrate was collected, concentrated and purified by column chromatography to obtain ethyl (S)-2,4-dimethyl-5-(2-oxo-2-((1,1,1-trifluoropropan-2-yl)amino)acetyl)-1H-pyrrol-3-carboxylate (0.5 g). MS (ESI-, [M–H]$^-$) m/z: 333.4.

Step D: Ethyl (S)-2,4-dimethyl-5-(2-oxo-2-((1,1,1-trifluoropropan-2-yl)amino)acetyl)-1H-pyrrol-3-carboxylate (300 mg), MeOH (2 mL) and a solution of NaOH (72 mg) in water (1 mL) were added to a reaction flask. After the addition, the reaction solution was heated to 80° C. and reacted overnight. After the reaction was completed, the reaction mixture was concentrated, then water (20 mL) and EA (60 mL) were added. The aqueous phase was separated, and the organic phase was washed with water (30 mL) and separated. The aqueous phases were combined, adjusted to about pH 3 by adding 2 N hydrochloric acid, and extracted with EA (100 mL×2). The mixture was separated, and the organic phase was concentrated to obtain (S)-2,4-dimethyl-5-(2-oxo-2-((1,1,1-trifluoropropan-2-yl)amino)acetyl)-1H-pyrrol-3-carboxylic acid (230 mg). MS (ESI-, [M–H]$^-$) m/z: 305.4.

Step E: (S)-2,4-dimethyl-5-(2-oxo-2-((1,1,1-trifluoropropan-2-yl)amino)acetyl)-1H-pyrrol-3-carboxylic acid (230 mg), DMF (5 mL), HATU (428 mg) and DIPEA (194 mg) were sequentially added to a reaction flask at room temperature. After the addition, the mixture was stirred for 10 min, then 5-amino-2-fluorobenzonitrile (123 mg) was added. The reaction system was heated to 40° C. and reacted with stirring for 20 h. After the reaction was completed, water (20 mL) and EA (60 mL) were added. The mixture was separated, dried over anhydrous sodium sulfate and filtered. The filtrate was collected, concentrated by rotary evaporation and purified by column chromatography to obtain (S)-N-(3-cyano-4-fluorophenyl)-2,4-dimethyl-5-(2-oxo-2-((1,1,1-trifluoropropan-2-yl)amino)acetyl)-1H-pyrrol-3-formamide (180 mg). $^1$H NMR (500 MHz, DMSO-d$_6$): δ12.05 (s, 1H), 10.20 (s, 1H), 9.49 (d, J=9.0 Hz, 1H), 8.20 (dd, J=6.0, 2.5 Hz, 1H), 7.98-7.91 (m, 1H),7.53 (t, J=9.0 Hz, 1H), 4.78-4.67 (m, 1H),2.40 (s, 3H), 2.32 (s, 3H), 1.34 (d, J=7.0 Hz, 3H). MS (ESI-, [M–H]$^-$) m/z: 423.0.

Figure 2:
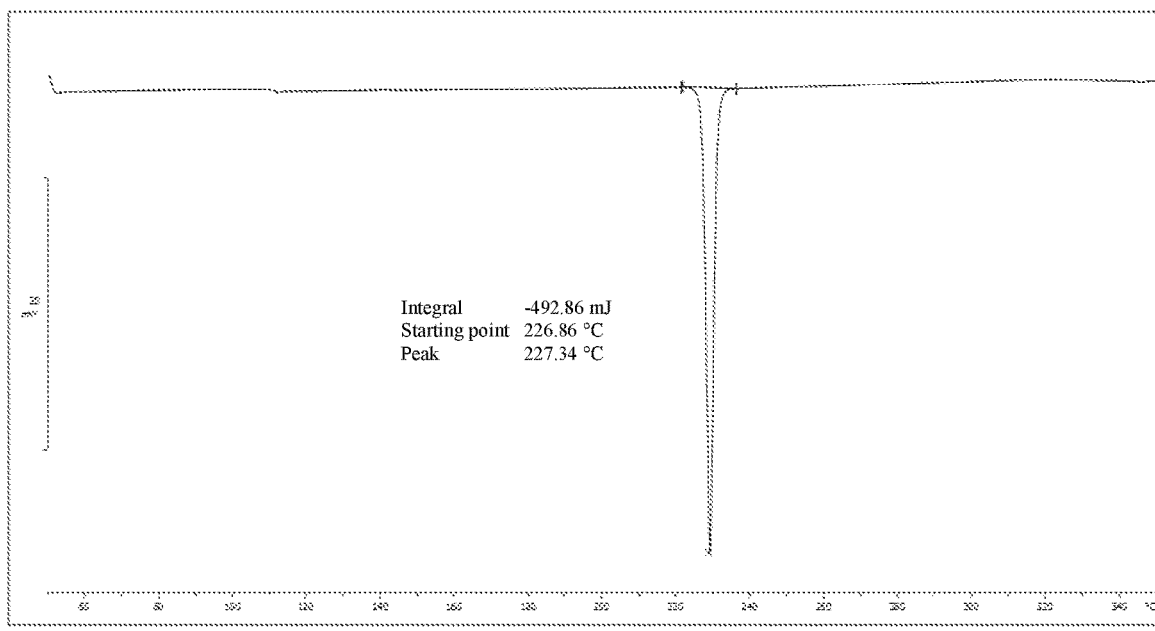
FIG. 2 is a DSC pattern of the crystalline form A of the compound of formula I.

Example 2. Preparation of Crystalline Form I of Compound of Formula A 500 mg of the compound of formula I was added to 25 mL of anhydrous methanol. The mixture was stirred at room temperature and heated to 60° C. to give a clarified solution. The resulting solution was cooled to room temperature and transferred into an ice-water bath. A large amount of white solid was precipitated. The mixture was filtered, and the filter cake was rinsed with anhydrous methanol and dried by air blasting at 70° C. for 8 h to obtain an off-white solid of the crystalline form A of the compound of formula I (300 mg). The sample was subjected to XRPD as shown in FIG. 1 and to DSC as shown in FIG. 2.

Experimental Example 1. Stability Assay of Crystalline Form 1.1. Preparation of Samples 500 mg of the crystalline form A of the compound of formula I prepared in Example 2 was placed in a dry and clean container, and evenly spread in a thin layer as the test sample. The sample was completely exposed to experimental conditions of influential factors (40° C., 60° C., 75% RH, 92.5% RH, high temperature and high humidity (40° C., 75% RH)). Samples were taken for analysis on day 10. The samples were completely exposed to illumination (visible light of 1,200,000 Lux·hr, UV of 216 W·hr/m$^2$) at room temperature.

1.2. Chromatographic Conditions

Chromatographic column: Waters XBridge Shield RP18 (4.6 mm×150 mm, 3.5 μm).

The water content was measured by a Mettler V20 system.

1.3. Preparation of Sample Solution

About 12.5 mg of the sample was dissolved with an appropriate amount of a mixed diluent of acetonitrile-water (70:30) for content assay of related substance.

TABLE 2

Results of stability assay

| Observation items | Day 0 | High temperature (40° C.), 10 days | High temperature (60° C.), 10 days | High humidity (75% RH), 10 days | High humidity (92.5% RH) 10 days | Illumination, 10 days | High temperature and high humidity (40° C., 75% RH), 10 days |
|---|---|---|---|---|---|---|---|
| Related substance$^a$ (%) | 0.57 | 0.65 | 0.65 | 0.63 | 0.65 | 0.64 | 0.63 |
| Water (%) | 0.13 | 0.17 | 0.16 | 0.15 | 0.17 | 0.16 | 0.16 |

$^a$Related substance refers to the total impurities.

The results in Table 2 showed that the related substance and water in the crystalline form disclosed herein are stable under the aforementioned observation items, demonstrating that the crystalline form has good stability at high humidity, at high temperature or under illumination.

Experimental Example 2. In-Vitro Activity Study 2.1. In-vitro Inhibitory Activity Against HBV DNA in Cells A vial of HepG2.2.15 cells (Wuhan Institute of Virology) or HepAD38 cells in good condition and at logarithmic growth phase was washed once with 5 mL of PBS. 3 mL of pancreatin was added. The cells were digested at room temperature for 5 min, then 2 mL of pancreatin was discarded. The cells were further digested in a cell incubator for 10 min, and observed under a microscope (whether the cells are round in shape, and whether the cells are separated or adhered). 10 mL of complete medium was added to terminate the digestion. The cells was mixed using a pipette to obtain a single cell suspension. 10 μL of the cell suspension was loaded on a cell counter for counting, and diluted with the complete medium to adjust the cell density to 1×10$^5$ cells/mL. The cells were seeded on a 24-well plate (pre-coated with 50 μg/mL Collagen I solution) at 1 mL/well using a multi-channel pipette and cultured in a thermostatic CO$_2$ incubator for 48 h.

A solution of the compound dissolved in DMSO was diluted to 10 concentrations in a 2-fold gradient using complete medium. The cells were treated with the compound for 6 days with the media containing the compound refreshed every 72 h. The supernatant was discarded. 300 μL of lysis buffer (10 mM Tris-HCl, 1 mM EDTA, 1% NP-40) was added to each well. After the cells were lysed at room temperature for 10 min, DNA was extracted. HBV DNA in the intracellular viral capsid was measured by real-time fluorescent quantitative PCR. The inhibition rate was calculated according to the Ct value, and the EC$_{50}$ value was calculated by four-parameter fitting. The results are shown in Table 3 and Table 4.

TABLE 3

Results of anti-HBV activity assay in HepAD38 cells

| No. | EC$_{50}$ (nM) |
|---|---|
| Compound of fromula I | 24 |

TABLE 4

Results of anti-HBV activity assay in HepG2.2.15 cells

| No. | EC$_{50}$ (nM) |
|---|---|
| Compound of fromula I | 17.4 |

2.2. In Vitro Cytotoxicity

A vial of HepG2.2.15 cells (Wuhan Institute of Virology) in good condition and at logarithmic growth phase was washed once with 5 mL of PBS. 2 mL of pancreatin was added. The cells were incubated in a cell incubator for digestion, and observed at times under a microscope. 1 mL of pancreatin was discarded when the cells just fell off, leaving the residual liquid only. The cells were further incubated in the incubator at 37° C. for 8-15 min of digestion and observed under a microscope (whether the cells are round in shape, and whether the cells are separated or adhered). 5 mL of MEM medium was added for cell resuspension. The cell suspension was loaded on a cell counter for counting, and diluted with the complete medium to adjust the cell density to 2×10$^5$ cells/mL. The cells were seeded on a 96-well plate (pre-coated with 50 μg/mL Collagen I solution) at 100 μL/well using a multi-channel pipette and cultured in a thermostatic CO$_2$ incubator for 24 h. The compound was added, and the medium containing the compound was refreshed every 3 days. A medium containing 0.5% of DMSO but no compound was added to the control wells, and control wells of basal medium were set. After 6 days of treatment, CCK-8 was added at 10 μL/well, and after 1-2 h, the absorbance at 450 nm was measured with a plate reader. The inhibition rate and CC$_{50}$ were calculated. The results are shown in Table 5.

TABLE 5

| Cells | $CC_{50}(\mu M)$ | No. |
|---|---|---|
| HepG2.2.15 | >100 | Compound of fromula I |

2.3. CYP450 Enzyme Inhibition Study

A final incubation system of 500 μL contained 50 μL of human liver microsomes (protein concentration: 0.2 mg/mL, Corning), 1 μL of mixed specific substrates of CYP450 (CYP1A2, CYP2B6, CYP2C9, CYP2C19, CYP2D6, CYP3A4), 398 μL of PBS (pH 7.4), 1 μL of specific positive inhibitor (positive control) or test compound (in acetonitrile) and 50 μL of NADPH+MgCl$_2$. Samples were prepared in duplicate of 0.5 mL for each CYP450 subtype. For each tube, the 450 μL mixed solution of substrates and enzyme and the NADPH solution were separately pre-incubated at 37° C. for 5 min. The 50 μL mixed solution of NADPH+MgCl$_2$ was added for reaction. At 30 min, 50 μL of the mixture was taken and 300 μL of glacial acetonitrile containing an internal standard was added to terminate the reaction. Additionally, 2 blanks of 500 μL each were prepared in parallel without adding NADPH as the negative control group.

Sample pretreatment: 300 μL of glacial acetonitrile containing an internal standard was added to 50 μL of the incubated sample for precipitation. The mixture was vortexed for 5 min, and centrifuged (12000 rpm, 4° C.) for 10 min. 75 μL of supernatant was taken and diluted with 75 μL of ultrapure water. After being mixed well, 1 μL of the resulting sample was injected for analysis. The results are shown in Table 6.

TABLE 6

| | Each subtype IC$_{50}$ (μM) | | | | | |
|---|---|---|---|---|---|---|
| No. | 3A4 | 2D6 | 2C19 | 2C9 | 2B6 | 1A2 |
| Compound of formula I | >200 | 54 | 20 | >200 | >200 | 49 |

2.4. Plasma Protein Binding Assay

Preparation of plasma samples: 5 μL of test compound solution or positive control was added to 495 μL of blank plasma of various species (mouse, rat, dog, monkey and human) to obtain plasma sample solutions at plasma concentrations of 1 μM and 10 μM (in acetonitrile).

The pretreated dialysis membrane was loaded on a high-throughput equilibrium dialysis system. 100 μL of the plasma sample solution and PBS buffer were added to the two sides (sample side and buffer side) of the dialysis membrane respectively (n=3). The system was sealed with a patch and incubated at 37° C. overnight (100 rpm) to achieve dialysis equilibrium. 50 μL samples were taken from the sample side and the buffer side, and the reaction was terminated with glacial acetonitrile containing an internal standard.

Sample pretreatment: 450 μL of glacial acetonitrile containing an internal standard was added to 50 μL of the sample from the plasma side for precipitation. The mixture was vortexed for 5 min, and centrifuged (12000 rpm, 4° C.) for 10 min. 75 μL of supernatant was taken and diluted with 75 μL of ultrapure water. After being mixed well, 1 μL of the resulting sample was injected for analysis; 250 μL of glacial acetonitrile containing an internal standard was added to 50 μL of the sample from the PBS side for precipitation. The mixture was vortexed for 5 min, and centrifuged (12000 rpm, 4° C.) for 10 min. 75 μL of supernatant was taken and diluted with 75 μL of ultrapure water. After being mixed well, 2 μL of the resulting sample was injected for analysis. The results are shown in Table 7.

TABLE 7

| | | Binding rate (%) | | | | |
|---|---|---|---|---|---|---|
| No. | Concentrations | Human | Rat | Mouse | Dog | Monkey |
| Compound of formula I | 1 μM | 97.3 | 95.0 | 85.4 | 94.0 | 90.2 |
| | 10 μM | 97.3 | 95.3 | 85.5 | 93.9 | 90.5 |

Experimental Example 3. In Vitro Stability in Liver Microsome

A final incubation system of 300 μL contained 30 μL of liver microsomes (protein concentration: 0.15 mg/mL, Corning), 30 μL of NADPH+MgCl$_2$, 3 μL of substrate (in acetonitrile) and 237 μL of PBS. Samples were prepared in duplicate of 0.3 mL for each specie. For each tube, the 270 μL mixed solution of substrates and enzyme and the NADPH solution were separately pre-incubated at 37° C. for 5 min. The 30 μL mixed solution of NADPH+MgCl$_2$ was added for reaction. 50-μL samples were taken at 0 min, 10 min, 30 min and 60 min, and 300 μL of glacial acetonitrile containing an internal standard was added to the samples to terminate the reaction.

Sample pretreatment: 300 μL of glacial acetonitrile containing internal standard diazepam was added to 50 μL of the incubated sample for precipitation. The mixture was vortexed for 5 min, and centrifuged (12000 rpm, 4° C.) for 10 min. 75 μL of supernatant was added to a 96-well plate and diluted with 75 μL of ultrapure water. After being mixed well, 0.5 μL of the resulting sample was injected to a LC-MS/MS system for analysis. The results are shown in Table 8.

TABLE 8

| | In Vitro stability in liver microsomes | | |
|---|---|---|---|
| No. | Human liver microsomes Residual content after 60 min (%) | Rat liver microsomes Residual content after 60 min (%) | Mouse liver microsomes Residual content after 60 min (%) |
| Compound of formula I | 99 | 99 | 96 |

Experimental Example 4. In Vivo Drug Efficacy in Animals 4.1. Evaluation of Antiviral Effect in AAV Mouse Model Male C57BL/6 mice (Shanghai Lingchang Biotechnology Co., Ltd.) aged 6-8 weeks were selected, and rAAV8-1.3HBV virus (FivePlus, Beijing, adr subtype) was injected into the C57BL/6 mice via tail veins at a dose of 1×10$^{11}$ vg. Blood was collected from the orbit at week 2 and week 4 after the virus was injected. Serum was separated, and the expression level of HBeAg and HBsAg and the copy number of HBV DNA in serum were measured to determine whether the model was successfully constructed or not. Combining the quantitative detection results of serological HBeAg, HBsAg and HBV DNA, mice with the expression levels over $1\times10^4$ IU/mL for HBV DNA, $1\times10^3$ NCU/mL for HBeAg and $1\times10^3$ ng/mL for HBsAg were selected. The mice were divided into a blank control group, a vehicle control group and a test compound group. The treatment was given by oral gavage once daily for 3 weeks and interrupted for 1 week. During the study, blood was collected from the orbit every other week, and serum was separated. The content of DNA was detected by fluorescence quantitative PCR. The results are shown in Table 9 and Table 10.

TABLE 9

Reduction (log10) of HBV DNA level in serum (at a dose of 10 mpk)

| No. | Day 7 | Day 14 | Day 21 | Day 28 |
|---|---|---|---|---|
| Compound of formula I | 2.67 | 3.80 | 4.30 | 3.50 |

TABLE 10

Reduction (log10) of HBV DNA level in serum (at a dose of 1 mpk)

| No. | Day 7 | Day 14 | Day 21 | Day 28 |
|---|---|---|---|---|
| Compound of formula I | 2.49 | 3.41 | 3.65 | 3.25 |

4.2. Experimental Methodology for pAAV/HBV Model

Purified recombinant plasmid pAAV/HBV1.2 (10 μg) was dissolved in PBS and then injected into male C57BL/6 mice (Shanghai Lingchang Biotechnology Co., Ltd.) aged 6-8 weeks via tail veins within 3-8 s in an amount of about 10% of the body weight. 3 days after the plasmid was injected, blood was collected from the orbit and serum HBV DNA was detected. Mice with homogeneous serum DNA were selected and divided into a model control group, a vehicle control group and a test compound group. Mice were administered with a dose of 3 mg/kg by oral gavage once daily for 10 days. Serum was taken on days 0, 4, 7 and 10 after administration. The mice were sacrificed and liver tissues were collected on day 10. The copy number of HBV DNA in serum and liver was determined by a fluorescence quantitative PCR method. The results are shown in Table 11.

TABLE 11

Reduction (log10) of HBV DNA level in serum (at a dose of 3 mpk)

| No. | Day 4 | Day 7 | Day 10 |
|---|---|---|---|
| Compound of formula I | 2.95 | 4.13 | 2.71 |

Experimental Example 5. In Vivo Pharmacokinetics

Pharmacokinetic (PK) Study in Rats

SD rats (B&K Universal, Shanghai) of 180-220 g were randomized into groups of 3 after 3-5 days of acclimatization and administered with the compounds at a dose of 20 mg/kg by oral gavage.

The animals to be tested (SD rats) were fasted for 12 h before administration and fed 4 h after administration, and had free access to water before, after and during the experiment.

After administration, about 0.2 mL of blood was collected from the orbit at 0 min, 15 min, 30 min, 1 h, 2 h, 4 h, 6 h, 8 h, 10 h, 24 h, 30 h and 48 h. After anticoagulation with EDTA-K2, the blood samples were transferred to a centrifuge at 4° C. within 30 min and centrifuged at 4000 rpm for 10 min to separate the plasma. All the plasma samples were collected and immediately stored at −20° C. for testing.

50 μL of the plasma sample to be tested and standard curve sample were taken, and 500 μL of acetonitrile solution containing an internal standard (20 mg/mL diazepam) was added. The reaction system was shaken for 5 min and centrifuged at 12,000 rpm for 10 min. 75 μL of supernatant was taken and diluted with 75 μL of ultrapure water. After being mixed well, 1 μL of the resulting sample was taken for LC/MS/MS analysis. The results are shown in Table 12.

TABLE 12

| | No. Compound of formula I | |
|---|---|---|
| Route of administration and dosage | IV 5 mg/kg | PO 10 mg/kg |
| $T_{1/2}$ (h) | 52.8 | 45.6 |
| Vz (mL/kg) | 2.58 | NA |
| Cl (mL/h/kg) | 0.03 | NA |
| $C_{max}$ (ng/mL) | 3512 | 4111 |
| $AUC_{(0-48\ h)}$ (ng * h/mL) | 126939 | 254490 |
| $AUC_{(0-\infty)}$ (ng * h/mL) | 147701 | 283784 |
| F (%) | NA | 100% |

NA denotes not available.

The invention claimed is:

1. A crystal of a compound of formula I,

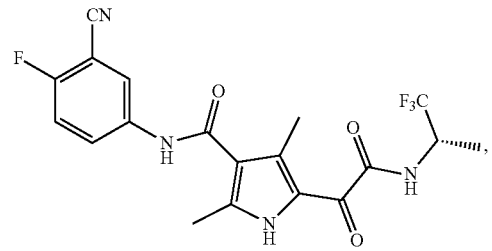

I wherein the crystal has characteristic diffraction peaks in an X-ray powder diffraction pattern at the following 2θ angles: 8.25±0.20°, 10.10±0.20°, 14.46±0.20°, 15.48±0.20° and 18.97±0.20°.

2. The crystal of the compound of formula I according to claim 1, wherein the XRPD pattern of the crystal is as shown in FIG. 1.

3. The crystal of the compound of formula I according to claim 1, wherein the crystal has a DSC curve having an endothermic peak at 227.34±5° C.

4. A crystalline form composition, wherein the crystal of the compound of formula I according to claim 1 accounts for 50% or more of the weight of the crystalline form composition.

5. A pharmaceutical composition, comprising a therapeutically effective amount of the crystal of the compound of formula I according to claim 1.

6. The crystal of the compound of formula I according to claim 1, wherein the crystal has characteristic diffraction peaks in an X-ray powder diffraction pattern at the following 2θ angles: 8.25±0.20°, 9.46±0.20°, 10.10±0.20°, 14.46±0.20°, 15.48±0.20°, 18.97±0.20°, 20.33±0.20° and 22.02±0.20°.

7. The crystal of the compound of formula I according to claim 1, wherein the crystal has characteristic diffraction peaks in an X-ray powder diffraction pattern at the following 2θ angles: 8.25±0.20°, 9.46±0.20°, 10.10±0.20°, 14.46±0.20°, 15.48±0.20°, 18.97±0.20°, 20.33±0.20°, 20.80±0.20°, 21.67±0.20°, 22.02±0.20°, 24.37±0.20°, 26.37±0.20° and 30.77±0.20°.

8. The crystal of the compound of formula I according to claim 1, wherein the crystal has characteristic diffraction peaks in an X-ray powder diffraction pattern at the following 2θ angles: 8.25±0.20°, 9.46±0.20°, 10.10±0.20°, 14.46±0.20°, 15.48±0.20°, 18.97±0.20°, 20.33±0.20°, 20.80±0.20°, 21.67±0.20°, 22.02±0.20°, 22.88±0.20°, 23.93±0.20°, 24.37±0.20°, 24.97±0.20°, 26.37±0.20°, 28.68±0.20° and 30.77±0.20°.

9. The crystalline form composition according to claim 4, wherein the crystal of the compound of formula I according to claim 1 accounts for 80% or more of the weight of the crystalline form composition.

10. The crystalline form composition according to claim 4, wherein the crystal of the compound of formula I according to claim 1 accounts for 90% or more of the weight of the crystalline form composition.

11. The crystalline form composition according to claim 4, wherein the crystal of the compound of formula I according to claim 1 accounts for 95% or more of the weight of the crystalline form composition.

12. A pharmaceutical composition, comprising a therapeutically effective amount of the crystalline form composition according to claim 5.

13. A method for treating a disease benefiting from the inhibition of capsid protein assembly, comprising administering to a mammal in need of such treatment a therapeutically effective amount of the crystal of the compound of formula I according to claim 1, wherein the disease benefiting from the inhibition of capsid protein assembly is a disease caused by hepatitis B virus infection.

14. A method for treating a disease benefiting from the inhibition of capsid protein assembly, comprising administering to a mammal in need of such treatment a therapeutically effective amount of the crystalline form composition according to claim 4, wherein the disease benefiting from the inhibition of capsid protein assembly is a disease caused by hepatitis B virus infection.

15. A method for treating a disease benefiting from the inhibition of capsid protein assembly, comprising administering to a mammal in need of such treatment a therapeutically effective amount of the pharmaceutical composition according to claim 5, wherein the disease benefiting from the inhibition of capsid protein assembly is a disease caused by hepatitis B virus infection.

16. A method for treating hepatitis B virus infection, comprising administering to a mammal in need of such treatment a therapeutically effective amount of the crystal of the compound of formula I according to claim 1.

* * * * *